US00PP13001P2

(12) United States Plant Patent
Sharma

(10) Patent No.: US PP13,001 P2
(45) Date of Patent: Sep. 24, 2002

(54) NEW GUINEA IMPATIENS PLANT NAMED 'PURITY'

(75) Inventor: Jagan N. Sharma, San L. Obispo County, CA (US)

(73) Assignee: Waller Genetics Incorporated, Guadalupe, CA (US)

( * ) Notice: Subject to any disclaimer, the term of this patent is extended or adjusted under 35 U.S.C. 154(b) by 25 days.

(21) Appl. No.: 09/585,562

(22) Filed: Jun. 1, 2000

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Purity, characterized by its white flower color, bright green leaves with no variegation, early flowering, long-lasting flowering, and self-branching and vigorous habit.

1 Drawing Sheet

The present invention relates to a new and distinctive cultivar of Impatiens plant, botanically known as *Impatiens Hawkeri*, commercially known as New Guinea Impatiens, and known by the cultivar name 'Purity'. Purity was developed in a controlled breeding program by crossing Waller Seedling No. 94-2A-70-1 (seed parent) with Waller Seedling No. 93-1A-600 (pollen parent). Both parents are proprietary breeding lines which have not been sold or made publicly available in this country.

Asexual reproduction carried out by Oglevee, Ltd. in Connellsville, Pa. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Purity has white flowers of White Group 155C as do both of Celebration White (patent pending) and Innocence (U.S. Plant Pat. No. 7,789).

2. Purity has a larger flower (6.0 to 6.5 cm) than that of Innocence (5.0 to 5.5 cm) but similar in size to the flower of Celebration White.

3. Purity has bright green leaves with no variegation while Innocence has bright green leaves with variegation and Celebration White has dull green leaves with no variegation.

4. Purity has 7 to 8 cm long leaves which are similar to Innocence and smaller than Celebration White (10 to 11 cm).

5. Purity has a light green spur similar to Innocence while Celebration White has a red-purple cast to the lower part of the spur.

6. Purity has a pure white mature flower bud while Celebration White has a pinkish cast to the flower bud.

7. Purity has no anthocyanin pigment in the stems while Celebration White and Innocence have some anthocyanin pigment, particularly around the nodes.

8. Purity has a more mounded growth habit than Celebration White and Innocence which are more upright in habit.

The accompanying photographic colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary dictionary significance are used.

Parentage: A controlled cross between female parent Waller Seedling No. 94-2A-70-1 and male parent Waller Seedling No. 93-1A-600.

Propagation:

(*A*) *Type cutting.*—Stem tip 15 mm long will develop to 4 to 5 cm long in 18 to 21 days.

(*B*) *Time to root*—8–10 days at 23° C. summer; 10–12 days at 20° C. winter.

(*C*) *Rooting habit.*—Heavy, fibrous.

Plant description:

*Form and habit of growth.*—Mounded to semi-upright, self-branching, intermediate to semi-tall in height; flowers open over the top of leaf canopy; continuous flowering; vigorous growing flowering herb. Average plant height is 25 to 30 cm, and average width is 40 to 45 cm. Internode length is 8 to 9 cm, but is highly variable, with a color of Yellow-Green Group 146C.

*Foliage description.*—Bright green with light green midrib and no leaf variegation. The young midrib underside is Yellow-Green Group 146C, and the mature midrib underside is Yellow-Green Group 148B. Mature leaf color is Yellow-Green Group 147A. Stem color is Yellow-Green Group 146C. (1) Size: 7 to 8 cm long and 3.0 to 3.5 cm wide on average mature leaf. (2) Shape: Lanceolate with acuminate apex and acute base. (3) Texture: Both upper and lower surfaces are glabrous. (4) Margin: Entire, with fine ciliate. (5) Color: Young foliage, top side is Green Group 137A, underside is Green Group 137C. Mature foliage, top side is Yellow-Green Group 147A, underside is Yellow-Green Group 147B. (6) Venation: Pinnate. Young venation underside is Yellow-Green Group 146B, and mature venation underside is Yellow-Green Group 146A.

*Branching.*—Lateral branches at base: 5 or more. Lateral branch is 18 to 21 cm, but is highly variable.

Flowering description:

*Flowering habits.*—Flowers continuously from leaf whorl in a progressively orderly manner with one flower per leaf axil. When the last flower in a whorl opens the first flower in the leaf whorl above starts to open. It takes 5 to 7 days for a mature bud to fully open and the flower may last two weeks or longer depending on the environment. The time to first flower is 50 to 55 days from rooted cutting. The flowers are self-cleaning.

*Natural flowering season.*—Indeterminant and continuous; quantity of flowering increases with increasing levels of light.

*Flower bud.*—Ellipsoidal; flowers perfect; spur is Yellow-Green Group 147C with a Yellow-Green Group 146B tip and is 5.5 cm long on average on mature bud, with the throat behind the ovary and originating from the major sepal. The pedicel is Yellow-Green Group 148D, the throat is Green-White Group 157D, and the bud is White Group 155C, just before opening.

*Flowers borne.*—On individual yellow-green 4.5 cm long pedicels from a whorl of usually five leaves. Flowering progressively around the whorls as buds and leaves develop. Leaf axils have one flower each.

*Quantity of flowers.*—Numerous because of self-branching nature of plant and the long-lasting flower characteristic.

*Diameter of flower.*—6.0 to 6.5 cm. Flower Depth: 5 mm.

*Petals.*—(1) Shape: Heart, keel petals are largest. (2) Color: Top side in winter when opening is White Group 155C with area of Green-White Group 157D in eye area and center of standard petal; no fading; underside is White Group 155C. (3) Number of petals: Five. (4) Size of petals: Standard: 3.5 cm wide by 3.0 cm long, two equal lobes with shallow cut. Wings: 3.25 cm wide by 3.0 cm long, two unequal lobes with moderate cut. Keel: 3.5 cm wide by 3.5 cm long, two unequal lobes with moderate cut.

*Reproductive organs.*—(1) Stamens: Five in number. (a) Anther: Hooded shape, White Group 155A. (b) Pollen color: White Group 155A. (2) Pistils: (a) Stigma: Five, segmented column, White Group 155C. (b) Style color: White. (c) Ovaries: Five in number, size is 6 mm when immature, Yellow-Green Group 146A.

*Fertility.*—The plants are fertile, but do not normally set seed under greenhouse conditions, unless in a controlled breeding program.

Disease resistance: No significant disease or insect problems seen to date.

OTHER IMPORTANT CHARACTERISTICS

1. Minimal fading of older flowers, large overlapping petals result in a round flower that produces an attractive floral display.

2. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus extending the growing season.

3. Is a self-branching, early flowering, vigorous growing plant that can quickly finish in a 15 to 25 cm container.

I claim:

1. A new and distinct variety of Impatiens plant named Purity, as illustrated and described.

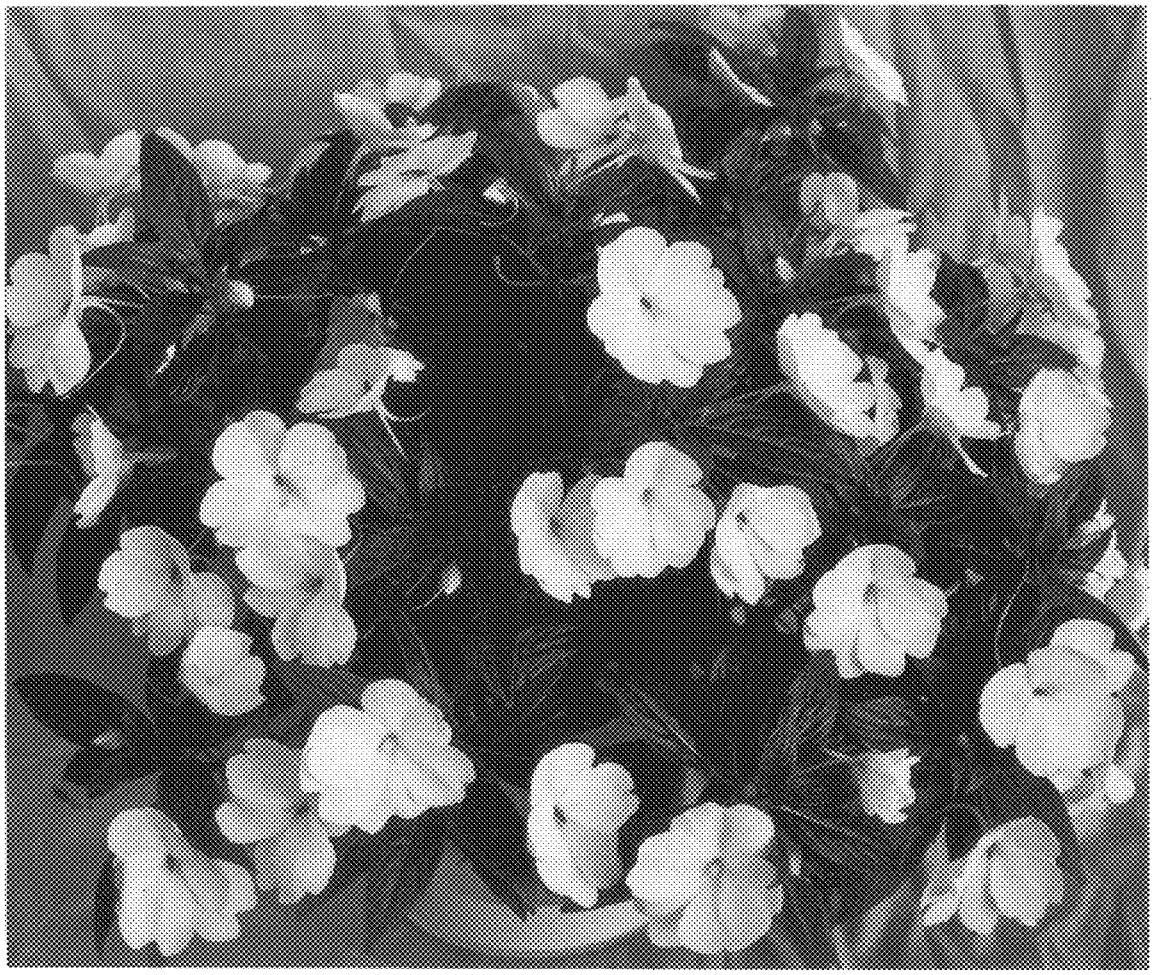

* * * * *